United States Patent
Cadet et al.

(10) Patent No.: US 6,208,251 B1
(45) Date of Patent: Mar. 27, 2001

(54) SYSTEM FOR MONITORING AND ASSISTING ISOLATED PERSONS, AND DEVICE FOR IMPLEMENTING THE SYSTEM

(76) Inventors: Pierre-Henri Cadet, Le Provence - 25 Avenue du Commandant Bret, 06400 Cannes (FR); Laurent Poyeton, 50 cours Vitton, Lyon (FR); Marc Vigneron, 32 Rue Chazieres, 69004 Lyon (FR)

( * ) Notice: Subject to any disclaimer, the term of this patent is extended or adjusted under 35 U.S.C. 154(b) by 0 days.

(21) Appl. No.: 09/319,006
(22) PCT Filed: Dec. 31, 1997
(86) PCT No.: PCT/FR97/02466
§ 371 Date: May 27, 1999
§ 102(e) Date: May 27, 1999
(87) PCT Pub. No.: WO98/29852
PCT Pub. Date: Jul. 9, 1998

(30) Foreign Application Priority Data

Dec. 31, 1996 (FR) .................................................. 96 16386

(51) Int. Cl.[7] .................................................. G08B 23/00
(52) U.S. Cl. .................. 340/573.1; 340/539; 340/689; 340/506; 600/513; 600/595; 600/310; 455/100; 455/521
(58) Field of Search .................... 340/573.1, 539, 340/689, 506; 600/513, 595, 310; 455/521, 100

(56) References Cited

U.S. PATENT DOCUMENTS

| | | | |
|---|---|---|---|
| 3,614,763 | * 10/1971 | Yannuzzi | 340/689 |
| 3,914,692 | 10/1975 | Seaborn, Jr. | 455/521 |
| 4,158,197 | * 6/1979 | Takagaki | 340/574 |
| 4,403,341 | * 9/1983 | Hata | 455/100 |
| 4,855,713 | * 8/1989 | Brunius | 340/506 |
| 4,858,622 | * 8/1989 | Osterweil | 600/595 |
| 4,899,133 | * 2/1990 | Bartlett | 340/573.1 |
| 5,146,206 | * 9/1992 | Callaway | 340/573.7 |
| 5,300,921 | * 4/1994 | Hoch et al. | 340/573.6 |
| 5,416,468 | * 5/1995 | Baumann | 340/573.1 |
| 5,515,858 | * 5/1996 | Myllymaki | 600/301 |
| 5,544,651 | * 8/1996 | Wilk | 600/310 |
| 5,670,944 | * 9/1997 | Myllymaki | 340/573.1 |
| 5,751,214 | * 5/1998 | Cowley et al. | 340/573.1 |
| 5,778,882 | * 7/1998 | Raymond et al. | 600/513 |
| 5,874,897 | * 2/1999 | Klempau et al. | 340/573.1 |
| 5,941,836 | * 8/1999 | Friedman | 600/595 |

FOREIGN PATENT DOCUMENTS

| | | |
|---|---|---|
| 4325087A1 | 2/1994 | (DE) . |
| 9408119 | 8/1994 | (DE) . |
| 522660 | 1/1993 | (EP) . |
| 2598535 | 11/1987 | (FR) . |

* cited by examiner

Primary Examiner—Benjamin C. Lee
(74) Attorney, Agent, or Firm—Wall Marjama & Bilinski

(57) ABSTRACT

This system for monitoring and assisting isolated persons comprises: a unit (15) decentralized at the desired location for monitoring and assisting the said persons, equipped with a receiver and intended to transmit an alarm signal, in particular by way of the switched telephone network (16), to one or more defined locations (17), in particular a monitoring centre, an emergency centre, neighbours or family; and a portable unit (1) intended to be carried by the said persons, incorporating an emitter which is intended to emit one or more signals in the direction of the decentralized unit (15), the said signals being intended to initiate the transmission of the alarm signal from the decentralized unit in the direction of the said defined locations, and additionally incorporating means (2, 3, 4) for detecting that the person carrying the device has fallen, these means being able to initiate the emission, by the emitter incorporated therein, of the said signals which are intended in turn to initiate the transmission of an alarm by the decentralized unit (15), these means of detection being of the gravimetric or accelerometric type.

12 Claims, 2 Drawing Sheets

SYSTEM FOR MONITORING AND ASSISTING ISOLATED PERSONS, AND DEVICE FOR IMPLEMENTING THE SYSTEM

The invention concerns a system for monitoring and assisting isolated persons, particularly in a domestic environment, that is to say in their home, but also in professional and industrial environments and in the course of leisure activities. It also concerns a device for implementing this system.

As regards the domestic environment, recent demographic studies carried out among the populations of the industrialized nations show a significant increase in the number of elderly persons and, consequently, in the number of infirm, poorly or handicapped persons, many of them living alone.

Moreover, whereas hospitalization of these persons for the slightest accident was for many years the norm, the current trend—with the objective of both optimizing the comfort of the patients and of reducing hospital costs—is as far as possible to encourage these persons to remain at home and to provide them either with a home visiting medical service or a monitoring service.

The problem posed by these persons remaining at home alone lies in the risks of illness, falls and other medical problems likely to affect these persons, and in their consequences if the said persons do not receive any help in good time.

Although periodic visits from friends, nurses and others afford some measure of security, and although the presence of the telephone makes it possible, if need be, to alert the competent authorities, some situations are without solution, especially in cases where the person has fainted or fallen, preventing him or her from using the telephone and, as a result, making it impossible to seek help.

In order to overcome this difficulty, systems of monitoring, assistance and/or surveillance have been proposed in which the person who is on their own permanently carries around a small unit which, when it is activated by the said person, initiates the emission of a signal in the direction of a centralized device, which is in turn able to initiate the triggering of an alarm at a monitoring centre, emergency centre and/or neighbours, and it does this by way of the switched telephone network. Such systems have been described, for example, in EP-A-0 522 660 and U.S. Pat. No. 3 914 692.

The proposed system thus unquestionably represents a step forward. However, it is not able to cover all the situations confronted by persons who are on their own, especially when these persons fall, causing loss of consciousness, or a state in which they are no longer capable of activating the unit they are carrying.

The same problems arise, especially in the industrial environment, and more particularly in hostile atmospheres, where the inhalation of toxic substances or exposure to potential hazards can lead to the person collapsing directly or as a result of fainting, and where remaining in such an atmosphere may prove damaging.

SUMMARY OF THE INVENTION

The object of the invention is to make available a system for monitoring and assisting isolated persons which takes these risks into account.

This system comprises:

a unit decentralized at the location for monitoring and assisting the said persons, equipped with a receiver and intended to transmit an alarm signal, for example by way of the switched telephone network, to one or more defined locations, in particular a monitoring centre, an emergency centre, neighbours or family;

and a portable unit intended to be carried by the said persons and incorporating an emitter which is intended to emit one or more signals in the direction of the decentralized unit, the said signals being intended to initiate the transmission of the alarm signal from the decentralized unit.

It is characterized in that the portable unit additionally incorporates means for detecting that the person carrying the device has fallen, these means being able to initiate the emission, by the emitter incorporated therein, of the said signals which are intended in turn to initiate the transmission of an alarm, these means for detecting a fall consisting of gravimetric means, such as in particular a mercury ball detector, or consisting of accelerometric means, such as a piezoelectric accelerometer.

In this way, it is possible to overcome the risk of persons being left in difficult or even critical situations, recent epidemiological studies showing that the number of these persons is relatively high and that the consequnces in terms of treatment are also critical.

In the context of the use of accelerometric detection means, the portable unit is advantageously equipped with three accelerometers, situated in three different directions, in such a way as to detect falls in the vertical plane, falls in the lateral plane and backward falls.

According to another characteristic of the invention, the portable unit is also equipped with a member which can be activated by the person carrying it and which is also intended to initiate, in a known manner, the transmission of an alarm by the decentralized unit. This member in most cases consists of a press-button, but it can of course consist of any other type of member performing an equivalent function. This member can, for example, be incorporated in a chain on which the portable unit is hung and which, when it is pulled off, initiates the transmission of the alarm.

According to another characteristic of the invention, the portable unit is equipped with a cutaneous impedance switch. In this way, the system is in the alert state only when the portable unit is in fact being worn by the user, the skin closing the alert circuit incorporated within the said portable unit.

According to another characteristic of the invention, the portable unit incorporates a circuit for recovery and storage of the electrocardiogram of the person in question. For this purpose, the portable unit is provided with a chain which is placed around the neck of the person in question, the said chain being equipped at its end, that is to say at the end opposite the area of attachment of the portable unit, and thus, when it is in place behind the neck, with contact electrodes which are able to take a first information item within the context of the recovery of the electrocardiogram. Moreover, the casing constituting the portable unit itself includes an electrode, situated on its rear face, so as to be situated level with the manubrium of the sternum of the individual, so as to permit, in association with the electrode for the neck, the acquisition of the data necessary for creating an electrocardiogram, the latter being stored in an integrated memory within the said casing. In this way, it is possible, in the event of the person fainting, or in the event of a fall being detected, to very quickly detect the cause of the faint or the fall, and, where appropriate, to provide suitable treatment as soon as possible.

BRIEF DESCRIPTION OF THE DRAWINGS

The way in which the invention can be put into practice and the advantages which derive from it will become clearer from the following embodiment which is given as a non-limiting example, with reference to the attached figures.

Thus, FIG. 1 shows a block diagram of a preferred embodiment of the portable unit of the invention. This portable unit is intended to be worn by the person, generally an elderly person or someone working in a hostile atmosphere.

DESCRIPTION OF THE INVENTION

Figure 1:
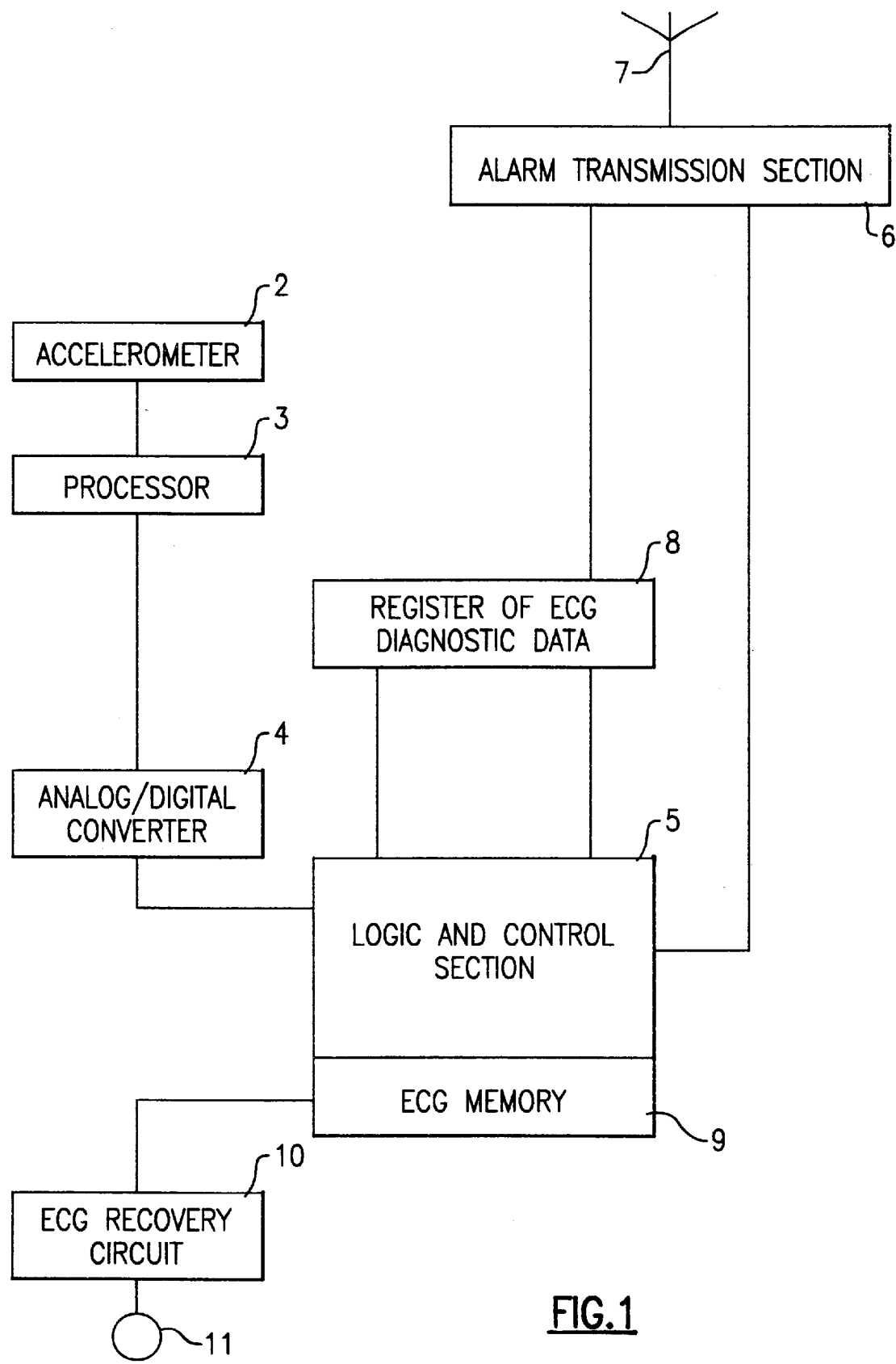
FIG. 1 is a diagrammatic representation, in the form of a block diagram, of the portable unit according to the invention.
Figure 2:
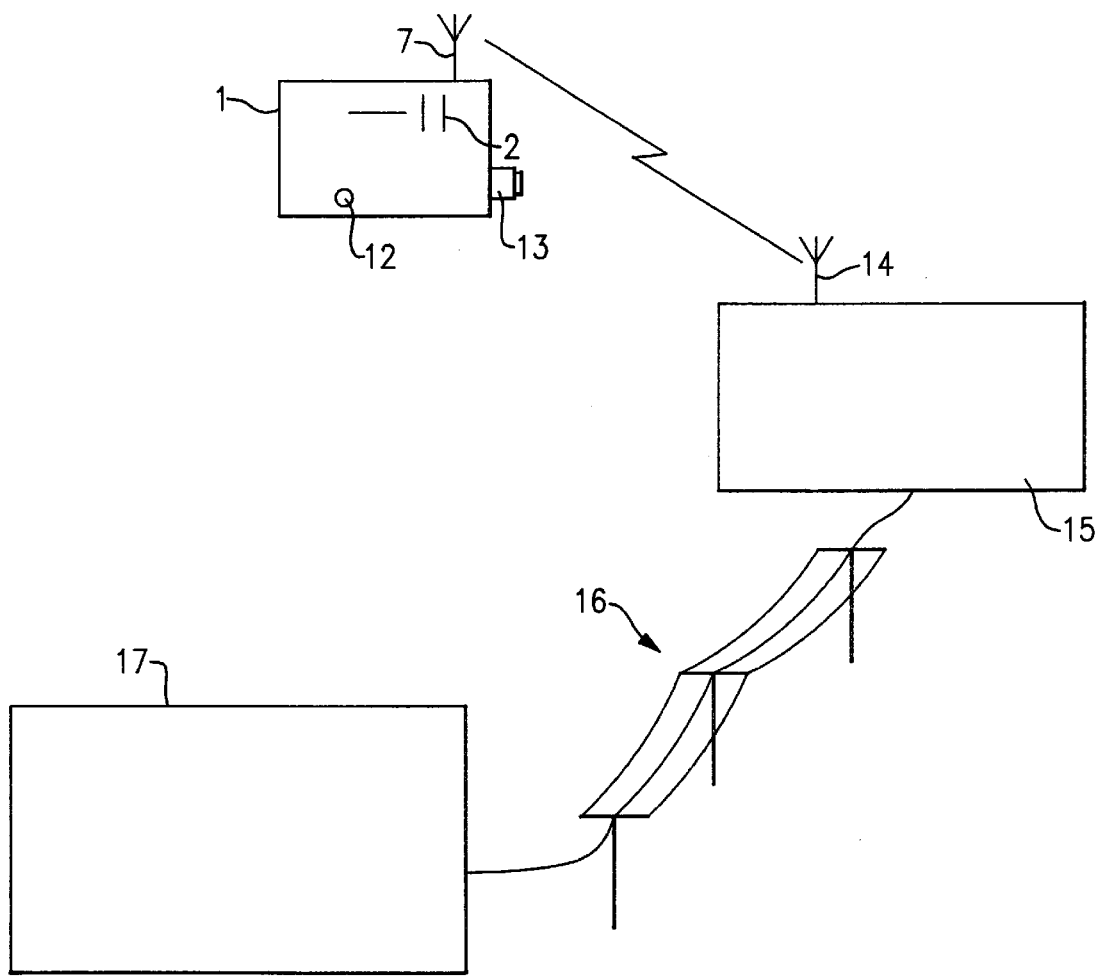
FIG. 2 is a diagrammatic representation of the functioning of the system according to the invention.

This portable unit is traditionally in the form of a casing (1) which is of a small size, for example 40 mm×50 mm, and light weight, incorporating a number of electronic components and, firstly, three accelerometers (2), as can be seen in FIG. 2. These accelerometers are calibrated to detect a fall in three planes, namely the vertical plane, the lateral plane and the antero-posterior plane. These accelerometers are also calibrated to emit a signal relating to a fall, for any movement undergoing an acceleration of about 2 g for a weight of about 50 kilos and a height of about one meter.

It is not the object of the invention to describe such an accelerometer which is well known per se. The latter traditionally consists of a piezo-electric crystal whose deformation leads to the creation of an electrical voltage, subsequently interpreted by an electronic circuit, in particular at a processor (3), then converted into a digital signal by means of an analog/digital converter (4), before being transferred to a logic and control section (5).

These accelerometers can also be of the electronic type with silicon.

The logic and control section typically includes software which, as a function of the signal transmitted by the accelerometer or accelerometers (2), is able to initiate the emission of a signal by way of an alarm transmission section (6) and an antenna (7) in the direction of a decentralized unit (14), typically a demodulator, which is placed in the home of the person in question and within range of the said portable unit. It will be appreciated that it is possible to parameterize the emission threshold of the alarm signal by acting on the software for processing the signal transmitted by the accelerometers, and, consequently, to give the whole arrangement a certain degree of reliability by overcoming false alarms.

This decentralized unit is known per se and, after receiving an alarm signal emitted by the portable unit, it is intended in turn to initiate the transfer or transmission of an alarm signal, for example by way of the switched telephone network (16), to a monitoring service, an emergency service and/or neighbours (17), in order to indicate that the person in question is at risk.

The accelerometer or accelerometers used, as well as the electronic network for transmission of the signal, are configured in such a way as to reduce to a minimum the risks of interference, in particular sudden movements, so as to make the detection of an incident or of an actual accident as reliable as possible.

The portable unit (1) is powered electrically by conventional batteries (not shown). Likewise, the decentralized unit (14) is powered electrically via the mains network. A plurality of batteries can be provided in order to keep the said decentralized unit in an operative state for several hours in the event of a circuit failure or power cut.

Moreover, the arrangement consisting of the portable unit (1) and of the decentralized unit (15) is clearly referenced in order to be identifiable by the emergency or monitoring centre (17) when an alarm is transmitted. For this purpose, a binary code specific to each of these arrangements is introduced into the memory of the logic and control section (5), this code being conveyed by the carrier wave of the telephone network in case of alarm.

According to one variant of the invention, the portable unit (1) is miniaturized in such a way that it is in the form of a microcircuit contained in an adhesive, and better known as a patch.

According to another variant, this portable unit is incorporated within a watch.

In all cases, and to ensure that the portable unit is indeed being worn by the user for whom it is intended, it incorporates an electrical circuit equipped with a cutaneous impedance switch. In other words, the electrical conduction of the skin is used to close the said electrical circuit, which then emits a signal, in particular in the direction of the central unit, indicating that the portable unit is operational and is being duly worn.

In a variant of the above embodiment, the said electrical circuit is additionally equipped with a delay time system, typically of a duration of about 30 seconds, so that in the absence of contact with the user's skin, and consequently in the case of the said circuit being open, no alarm signal is triggered, indicating that the portable unit is no longer being worn. This is particularly of interest when the portable unit is hung from a neck chain and is no longer in contact with the skin when the user leans over.

According to a preferred embodiment of the invention, the portable unit (1) also includes means which are able to permit the recording of an electrocardiogram of the patient. This recording is made possible, on the one hand, by combining a neck chain (not shown) with the portable casing constituting the portable unit, this neck chain incorporating at its upper end one or two detection electrodes, the simple contact of these electrodes with the neck allowing a measurement to be taken, and, on the other hand, by placing another measurement electrode on the back of the casing (1). For this purpose, the length of the chain is regulated so that the electrode on the back of the casing comes into contact with the patient substantially at the area of the manubrium of the sternum. In this way, means (11) are defined for acquisition of the data necessary for establishing an electrocardiogram (ECG) associated with a circuit for recovery (10) of the ECG. This circuit for recovery of the ECG (10) is also placed within the casing constituting the portable unit (1).

This electrocardiogram is permanently stored in a memory (9) associated with the logic and control section (5) by overwriting the previously stored electrocardiogram. The memory time is typically 15 minutes.

The logic and control section (5) is also equipped with a selector which is able to register the said electrocardiogram in a diagnostics register (8), in other words in a memory, in such a way as to allow the practitioner to analyse the electrocardiogram and consequently to detect the origin of the cause of the faint or fall, and, as a result, to provide the appropriate care more rapidly.

The electrocardiogram is advantageously analysed automatically in real time within the logic and control section in order to detect major bradycardia or tachycardia, by parameterizing a threshold which is not be exceeded, respectively a low-frequency threshold, for example 25 beats per minute, or high-frequency threshold, for example 150 beats per minute.

It then becomes possible to generate triggering of an alarm signal in the event of fainting or loss of consciousness, these being phenomena which induce a measurable variation in heart rate.

In addition, according to a development of the invention, the memory of the logic and control section (5) is charged with managing the dosage of one or more medicaments appropriate to the disease from which the wearer of the portable unit is suffering, possibly chronically. The content of this memory can be accessed by way of a reader equipped with a suitable connection, allowing the emergency services, where appropriate, to gain access to the information which is essential for the treatment that is to be performed.

According to the invention, the casing also includes a press-button (13) or the like which can be activated by the person wearing the portable unit (1), or by a third party, in order to trigger an alarm when necessary. This press-button can be replaced or complemented by an electrical member (not shown), for example incorporated in the closure device of the said chain, and closing the electrical circuit permitting the triggering of the alarm signal, this electrical member being activated by pulling off the chain holding the portable unit. In fact, with this possibility, triggering of the alarm signal can be made easier when the user is in a difficult situation, sometimes making it tricky to activate a traditional press-button. In addition, this makes it possible to eliminate the false alarms which result from inadvertently activating the press-button.

Advantageously, and with a view to ensuring the greatest possible safety of the isolated person, the system of monitoring and/or assistance according to the invention includes means making it possible to inform the said person that the alarm signal has indeed been transmitted to the monitoring centre, emergency centre or to the designated third parties. For this purpose, a signal is transmitted by way of the switched telephone network from the said centre or the third party or parties towards the decentralized unit (15), naturally after having transmitted the alarm to the service concerned, this signal being visualized, for example, by illumination of the light-emitting diode (12) on the portable unit (1), by vibration of a small buzzer (not shown), or by emission of a pre-recorded audio message, in such a way that the person in distress can see or hear the confirmation that the alarm signal has been properly triggered.

Moreover, in order to ensure that the system, in particular the portable unit (1)/decentralized unit (15) arrangement, is working correctly, these two units are advantageously equipped with a tester (not shown), which consists, for example, of a press-button that is not directly accessible, so as not to risk false manoeuvres, and whose activation generates an automatic test of the essential functions of the system, without causing transmission of an alarm. The correct functioning of the said arrangement can then be visualized, after triggering of the tester, by the illumination of a light-emitting diode of a colour different than that (12) indicating the correct transmission of the alarm signal.

The decentralized unit can of course be mounted on the wheelchair of a handicapped person. In this configuration, the system according to the invention fulfills its role perfectly, the interface with the switched network being at present fully mastered, especially by employing the developments used for cellular mobile phones.

In the same connection, it is also possible to use a locating interface incorporated within the portable unit and the decentralized unit, for example to permit identification and positioning by satellite—GPS system—by equipping the satellite with a complementary interface unit. This embodiment finds an application in cases where the user is mentally deficient, and where it is necessary to keep track of the individual.

A complete assembly is thus made available which is able to provide a sense of added security not just for persons living on their own, particularly in a domestic environment, but also for their family circle, since in almost all possible situations, particularly of distress, an alarm can be transmitted to the services or parties concerned. Moreover, such a system is widely applicable to persons working in isolation in a hostile atmosphere.

All the benefits of such a system and of the associated portable unit will thus be readily appreciated.

What is claimed is:

1. Apparatus for monitoring an individual's condition and summoning help when a potentially dangerous condition is sensed, said apparatus including a decentralized unit containing a receiver, a portable unit capable of being carried by an individual that contains an emitter means for transmitting one or more output signals to the receiver of said decentralized unit, said output signals being arranged to automatically trigger an alarm signal by said decentralized unit that is sent by a switched telephone network to one or more receiving centers, said portable unit further including three piezoelectric accelerometers adapted to sense falls by an individual carrying the portable unit in a vertical direction, and in a lateral direction, and in a backward direction, and in response thereto initiating a transmission by said emitter means.

2. The apparatus of claim 1 wherein said portable unit further includes manually activating means for initiating an output signal.

3. The apparatus of claim 2 wherein said manually activating means comprises a push button switch that can be cycled by an individual carrying or wearing said portable unit.

4. The apparatus of claim 2 that further includes a neck chain for carrying said portable unit and said activating means is mounted in a closure device for joining both ends of said chain.

5. The apparatus of claim 1 that further includes adhesive means for affixing the portable unit to the skin of an individual.

6. The apparatus of claim 1 that further includes an electrical circuit that is closed by a cutaneous impedance switch that is arranged to close when said portable unit is being worn or carried by an individual.

7. The apparatus of claim 1 that further includes circuit means for detecting and storing electrocardiogram data from an individual wearing or carrying said portable unit.

8. The apparatus of claim 7 that further includes a neck chain that is capable of being worn or carried by an individual for supporting the portable unit, wherein said portable unit further includes a casing containing contact electrodes on its rear face for acquiring electrocardiogram data from an individual wearing the chain when the casing is placed over the individual's manubrium of the sternum, said data being stored by an integrated memory within said casing.

9. The apparatus of claim 8 wherein said portable unit further includes a logic and control section for analyzing the acquired electrocardiogram data to detect cardiac dysfunctions, and in response thereto triggering an alarm signal.

10. The apparatus of claim 1 wherein the decentralized unit is mounted upon a wheelchair capable of carrying an individual wearing said portable unit, said decentralized unit containing a switched telephone network for a mobile unit.

11. The apparatus of claim 1 that further includes means for position finding by a satellite.

12. The apparatus of claim 1 that further includes means for informing the individual wearing or carrying the portable unit that an alarm signal has been sent by the decentralized unit to one or more receiving centers.

* * * * *